(12) United States Patent
Yamamoto

(10) Patent No.: US 7,748,388 B2
(45) Date of Patent: Jul. 6, 2010

(54) ENDOSCOPIC INJECTABLE PREPARATION

(76) Inventor: Hironori Yamamoto, 2-15-13, Gion, Minamikawachi-machi, Kawachi-gun, Tochigi (JP) 329-0434

(*) Notice: Subject to any disclaimer, the term of this patent is extended or adjusted under 35 U.S.C. 154(b) by 1475 days.

(21) Appl. No.: 10/466,090

(22) PCT Filed: Jan. 18, 2002

(86) PCT No.: PCT/JP02/00333

§ 371 (c)(1),
(2), (4) Date: Jul. 11, 2003

(87) PCT Pub. No.: WO02/056914

PCT Pub. Date: Jul. 25, 2002

(65) Prior Publication Data

US 2004/0059066 A1    Mar. 25, 2004

(30) Foreign Application Priority Data

Jan. 19, 2001   (JP)   ............................ 2001-011524

(51) Int. Cl.
*A61B 19/00*   (2006.01)
(52) U.S. Cl. ........................................ 128/898; 606/46
(58) Field of Classification Search ................. 128/898; 514/54; 606/36, 47, 110–113, 46; 600/101, 600/104
See application file for complete search history.

(56) References Cited

U.S. PATENT DOCUMENTS

| | | | | |
|---|---|---|---|---|
| 4,940,468 A | * | 7/1990 | Petillo | 606/170 |
| 5,542,948 A | * | 8/1996 | Weaver et al. | 606/113 |
| 5,651,788 A | | 7/1997 | Fleischer et al. | |
| 5,997,547 A | * | 12/1999 | Nakao et al. | 606/114 |
| 5,998,384 A | | 12/1999 | Shimada et al. | |
| 6,004,299 A | * | 12/1999 | Arai et al. | 604/218 |

(Continued)

FOREIGN PATENT DOCUMENTS

EP    0 974 320 A1    1/2000

(Continued)

OTHER PUBLICATIONS

Kenichi et al., "Energy Source for Minimally Invasive Therapy", 398 Sogo Rinsho (General Clinic), vol. 48, No. 3, 1999 (Transl.).

(Continued)

*Primary Examiner*—William H. Matthews
(74) *Attorney, Agent, or Firm*—Browdy and Neimark, PLLC

(57) ABSTRACT

It is disclosed that a long elevation time is obtained and the efficiency of resection can be improved by providing an endoscopic injectable preparation using high molecular weight hyaluronic acid having an average molecular weight of 1,500,000 to 3,000,000 or its salt.

In treating early cancer or other neoplastic mucosal lesion, the lesion is resected with handling of an endoscope ("endoscopic mucosal resection") instead of performing a major surgical operation such as laparotomy, thoracotomy or organ excision. In performing endoscopic mucosal resection, physiological saline, or a solution of low molecular weight hyaluronic acid or its salt is injected into a stratum below the site of lesion scheduled for resection to elevate the site of lesion, thereby increasing the efficiency of resection. To raise the efficiency of endoscopic mucosal resection, however, the development of an injectable preparation presenting a longer elevation time and requiring a low injection pressure has been desired.

4 Claims, 1 Drawing Sheet

U.S. PATENT DOCUMENTS

| | | | |
|---|---|---|---|
| 6,007,546 | A | 12/1999 | Snow et al. |
| 6,190,695 | B1 * | 2/2001 | Hoshino et al. ............. 424/464 |
| 6,210,416 | B1 | 4/2001 | Chu et al. |
| 6,319,260 | B1 | 11/2001 | Yamamoto |

FOREIGN PATENT DOCUMENTS

| | | |
|---|---|---|
| JP | 63-028398 | 2/1988 |
| JP | 4-39997 B2 | 5/1988 |
| JP | 63-123392 B2 | 5/1988 |
| JP | 6-30604 B2 | 4/1994 |
| JP | 08-188534 A | 7/1996 |
| JP | 2001-192336 A | 7/2001 |
| JP | A 2001-192336 | 7/2001 |

OTHER PUBLICATIONS

Yamamoto et al., "0-5 Attempt at Endoscopic Mucosal Resection Using Sodium Hyaluronate", 55th "General Meeting Association of Gastrornterological Engdoscopy",vol. 40 (Suppl. 1), 1998 (Transl.).

Hirao, Masanori, et al., "Endoscopic Resection of Early Gastric Cancer and Other Tumors with Local Injection of Hypertonic Saline-epinephrine", *Gastrointestinal Endoscopy*, vol. 34, No. 3, 1988, p. 264-269.

Makuuchi, Hiroyasa, et al., "Endoscopic Mucosal Resection for Early Esophageal Cancer by the EEMR-tube Method", *Stomach and Intestine*, vol. 28, No. 2, 1993, p. 153-159 (Partial Translation).

Sunada, Fumiko, "Two Cases of Endoscopic Muscal Resection of Rectal Carcinoid Wherein Aqueous Sodium Hyaluronate Is Used", *Preprint for 57th Conference of Japan Gastroenterological Endoscopy Society*, Abstract No. 305, May 11, 1999 (Translation).

Yamamoto, H. et al., "A Novel Method of Endoscopic Mucosal Resection (EMR) Using a Mucinous Substance of Sodium Hyaluronate", G2922, *Gastroenterology*, vol. 114, No. 4, May 20, 1998.

Yamamoto, Hironori et al., "Endoscopic Mucosal Resection Using Sodium Hyaluronate—for a Reliable en bloc Resection", Preprint for the 57th *Conference of Japan Gastroenterological Endoscopy Society*, Abstract No. 489, May 11, 1999 (Translation).

Yamamoto, Hironori et al., "Endoscopic Mucosal Resection Using Sodium Hyaluronate", *Preprint for 56th Conference of Japan Gastroenterological Endoscopy Society*, VTR Session, No. VS-2, Nov. 20, 1998 (Translation).

Conio, et al., "Comparative Performance in the Porcine Esophagus of Different Solutions Used for Submucosal Injection" Gastrointestinal Endoscopy. 2002; vol. 56 (4): 513-516.

Yamamoto, et al., "Success Rate of Curative Endoscopic Mucosal Resection with Circumferential Mucosal Incision Assisted by Submucosal Injection of Sodium Hyaluronate" Gastrointestinal Endoscopy. 2002; vol. 56 (4): 507-512.

Yamamoto, et al., "Successful EnBloc Resection of Large Superficial Tumors in the Stomach and Colon Using Sodium Hyaluronate and Small-Caliber-Tip Transparent Hood" Endoscopy. 2003; vol. 35 (8): 690-694.

Yamamoto, et al., "Successful EnBloc Resection of A Large Superficial Gastric Cancer by Using Sodium Hyaluronate and Electrocautery Incision Forceps" Gastrointestinal Endoscopy.2001; vol. 54 (5): 629-632.

H. Yamamoto et al., "A successful single-step endoscopic resection of a 40 millimeter flat-elevated tumor in the rectum: endoscopic mucosal resection using sodium hyaluronate", Gastrointestinal Endoscopy vol. 50, No. 5, pp. 701-704, 1999.

H. Yamamoto et al., "A novel method of endoscopic mucosal resection using sodium hyaluronate", Gastrointestinal Endoscopy vol. 50, No. 2, pp. 251-256, 1999.

Supplemental European Search Report issued in Application No. EP 02 71 5812 (Aug. 2009).

H. Yamamoto et al "A successful single-step endoscopic resection of a 40 millimeter flat-elevated tumor in the rectum: endoscopic mucosal resection using sodium hyaluranate" Gastrointestinal Endoscopy 50(5): 701-704 (1999H. ).

T. Kikuchi et al "Effect of high molecular weight hyaluronan on cartilage degeneration in a rabbit model of osteoarthritis" Osteoarthritis and Cartilage 4(2): 99-110 (1996).

K. Tamoto et al "Effects of high-molecular-weight hyalurontes on the functions of guinea pig polymorphonuclear leukocytes" Seminars in Arthritis and Rheumatism (Suppl 1) 22(6): 4-8 (1993).

Hempel et al "Pharmazeutische Stoffliste" 1-8 ABDATA Pharma-Daten-Service, p. 147 Abstract (1996).

* cited by examiner

ENDOSCOPIC INJECTABLE PREPARATION

TECHNICAL FIELD

This invention relates to an endoscopic injectable preparation which is used to elevate a mucosal tissue of the stomach or intestine when resecting the mucosal tissue using an endoscope.

BACKGROUND ART

A method of endoscopically resecting a small lesion, such as a polyp or cancer, formed on the mucosa of the gastrointestinal tract, such as the stomach or intestine, without performing laparotomy (the method is called endoscopic mucosal resection), is performed clinically. During this operation, the site of the mucosal lesion does not necessarily protrude clearly. Moreover, the surface of the mucosa is slippery. Thus, resecting the lesion by remote control while observing it through the endoscope involves corresponding technical difficulty, and may cause a risk, such as the remaining lesion after resection, or a surgery-associated complication such as bleeding or perforation.

To improve the resection efficiency, operability and safety of endoscopic mucosal resection, it has been common practice to inject physiological saline into the stratum below the site scheduled for resection, thereby elevating and protruding (hereinafter referred to simply as "elevating" or "elevation" according to the context) the lesion, and resect the lesion. According to this method, however, the elevated site is easily deformable upon compression for resection. Also, the level of the elevation is so low that the elevation dissipates rapidly over time and disappears. Thus, it has been difficult to resect the targeted site reliably.

Alternatively, a hypertonic saline solution or a 50% glucose solution has been used for more persistent elevation. However, the elevation sustaining effect of such a hypertonic solution is not very high, and is even injurious to the tissue. The application of the hypertonic solution may cause perforation to the large intestine with a small wall thickness, and is problematical in safety. Under these circumstances, the inventor of the present invention previously proposed the injection of low molecular weight hyaluronic acid with an average molecular weight of about 800,000 (Gastrointest. Endosc. 50(5), 701-704, 1999; Gastrointest. Endosc. 50(2), 251-256, 1999; Japanese Patent Application No. 2000-37240). Hyaluronic acid, existent in large amounts in vivo, has a high molecular weight, and shows high viscosity at low concentrations, thus minimally affecting osmotic pressure. When diluted with physiological saline, therefore, hyaluronic acid can form a preparation isotonic to body fluids, and can give a solution with in vivo safety which is injected submucosally during endoscopic mucosal resection (EMR).

The above method, proposed by the present inventor, improves the level of elevation and the duration of elevation of the lesion, and increases the efficiency of resection, as compared with the conventional method. However, the duration of elevation of the lesion is at most about 10 to 20 minutes under favorable conditions (concentration of 0.5 w/v %). This elevation time is not entirely satisfactory when a surgical operation takes time as in resecting a lesion of 20 mm or larger in one piece. Development of an injectable preparation presenting a longer elevation time has been desired.

A parenteral solution (injectable preparation as a solution) for injecting high molecular weight hyaluronic acid into the intra-articular space is known (Japanese Unexamined Patent Publication No. 1996-188534). However, an injection needle for this injectable preparation is so short in length that the injection pressure of hyaluronic acid is not very problematical. In the case of an injection needle for an endoscope, on the other hand, the effective length of the tube of the injection needle is usually as long as 1,000 mm or more, so that the injection pressure of the injectable preparation is a major problem from the point of view of operability.

Thus, the development of an injectable preparation, which can prolong the elevation time as stated earlier, does not involve too high an injection pressure, and is not problematical in operability, is desired.

DISCLOSURE OF THE INVENTION

The present inventors conducted in-depth studies, and developed an injectable preparation presenting a prolonged time of injection-induced elevation of a lesion and having excellent operability during injection.

An increase in the concentration of low molecular weight (about 800,000) hyaluronic acid is conceivable as a method for prolonging the elevation time of a mucosal tissue portion scheduled to be resected. However, if the concentration of hyaluronic acid is increased to about 1 w/v %, the elevation time can be extended to about 30 minutes, but the viscosity of the hyaluronic acid solution is markedly increased. This results in a high injection pressure during injection through an endoscopic injection needle, thus making injection difficult. Hence, hyaluronic acid at an increased concentration is difficult to use practically from the viewpoint of operability.

Alternatively, the use of high molecular weight (about 1,200,000 or more) hyaluronic acid may be contemplated for prolongation of the elevation time. However, this use was expected to make the injection pressure higher than the use of low molecular weight hyaluronic acid.

When high molecular weight hyaluronic acid is used, lowering its concentration can be conceived in order to make the injection pressure low. For example, in order to obtain an injection pressure comparable to that produced by use of low molecular weight hyaluronic acid, one idea would be to lower the concentration of high molecular weight hyaluronic acid to about a half or less. In this case, it was predicted that deformation of the elevated site when compressed would be marked, and the extension of the elevation time would not be great.

Study with the actual use of hyaluronic acid having a particular high molecular weight, however, upset the initial expectation. Although nearly equal in concentration to low molecular weight hyaluronic acid, the particular high molecular weight hyaluronic acid was found to be injectable at an injection pressure sufficiently usable for practical purposes, and was also found to cause no deformation of the elevated site during compression and to be able to improve the extension of the elevation time. The reason for this has not necessarily been clarified, but one of the causes may be that the physicochemical properties, such as viscoelasticity and friction coefficient, of low molecular weight hyaluronic acid and those of high molecular weight hyaluronic acid greatly differ from each other, with a molecular weight of about 1,000,000 to 1,200,000 as the borderline. That is, the high molecular weight hyaluronic acid has higher viscoelasticity and lower friction coefficient, and thus is presumed to be movable at an unexpectedly low pressure through a cylinder such as an injection tube.

The present inventor also paid attention to the facts that viscoelasticity was decreased by the existence of a salt in hyaluronic acid, and that this phenomenon was remarkable especially in high molecular weight hyaluronic acid. The inventor made various studies on hyaluronic acid which would show viscoelasticity giving an appropriate injection pressure, and which would be able to prolong the elevation time, at about a salt concentration (0.9% NaCl) used in an actual surgical operation. As a result, they found that the intended objects could be achieved when a salt concentration was 0.8 to 1%, preferably about 0.9%, and hyaluronic acid having a particular molecular weight, namely, a viscosity-average molecular weight of 1,500,000 to 3,000,000, preferably 1,900,000 to 2,200,000, was used at a concentration of 0.05 to 0.8 w/v %, preferably 0.1 to 0.7 w/v %, particularly preferably 0.3 to 0.5 w/v %. Based on this finding, the inventor accomplished the present invention.

Figure 1:
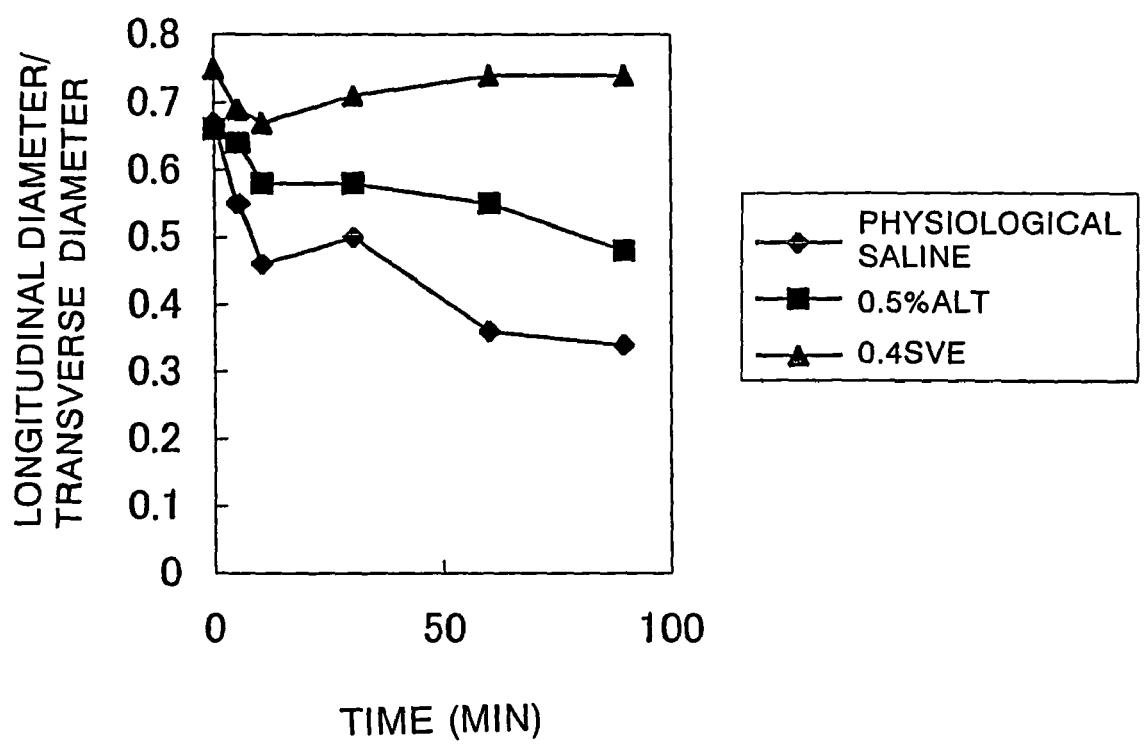
FIG. 1 is a graph showing the durations of mucosal elevations of a porcine resected stomach determined by observing the sectional shape of the elevated mucosa by an ultrasonic tomograph, as parameters representing the degrees of the mucosal elevations created by Example 2.

More concrete embodiments of the present invention are enumerated as follows:

A gelled high viscosity substance-containing endoscopic injectable preparation, used for a method comprising injecting a gelled high viscosity substance into a predetermined mucosal tissue to elevate the mucosal tissue, and endoscopically resecting the mucosal tissue portion, characterized in that the gelled high viscosity substance is hyaluronic acid having a viscosity-average molecular weight of 1,500,000 to 3,000,000 or a salt thereof.

The injectable preparation containing 0.05 to 0.8 w/v % of the gelled high viscosity substance.

The injectable preparation having the gelled high viscosity substance dissolved in an aqueous solution containing 0.8 to 1% of sodium chloride.

The injectable preparation wherein the gelled high viscosity substance is hyaluronic acid obtained by microbial fermentation and having a viscosity-average molecular weight of 1,500,000 to 3,000,000 or a salt thereof.

The injectable preparation wherein a hyaluronic acid-producing microorganism is *Streptococcus equi*.

The injectable preparation wherein an endoscopic injection needle for injecting the endoscopic injectable preparation has a diameter of 20 to 22 G, and the effective length of a tube of the injection needle is 1,000 mm or more.

The injectable preparation adjusted such that the injection pressure of the injectable preparation when injected through an endoscopic injection needle having a diameter of 20 to 22 G, and having a tube with an effective length of 1,000 mm or more is 0.5 to 4 atmospheres.

The injectable preparation adjusted such that the inflow rate of the injectable preparation when injected at a pressure of 2 to 3 atmospheres through an endoscopic injection needle having a diameter of 20 to 22 G, and having a tube with an effective length of 1,000 mm or more is 0.05 to 0.1 ml/sec.

The present invention will be described further below.

EMBODIMENTS OF THE INVENTION

In the present invention, hyaluronic acid having a viscosity-average molecular weight of 1,500,000 to 3,000,000, preferably 1,900,000 to 2,200,000 is used. In the present invention, it is preferred to use high molecular weight hyaluronic acid obtained by microbial fermentation, especially high molecular weight hyaluronic acid produced by *Streptococcus equi* (e.g., Japanese Patent Publication No. 1992/39997, Japanese Patent Publication No. 1994/30604), each of the high molecular weight hyaluronic acids having a viscosity-average molecular weight in the above range.

Such high molecular weight hyaluronic acid can be used in an amount of 0.05 to 0.8 w/v %, preferably 0.1 to 0.7 w/v %, particularly preferably 0.3 to 0.5 w/v %, in the injectable preparation of the present invention. If the concentration is lower than this range, deformation of the elevated site when compressed tends to occur, operability during resection declines, and the effect of extending the elevation time cannot be expected. If the concentration is higher than the above range, the injection pressure will be high and the operability during injection decreases. Moreover, such high molecular weight hyaluronic acid may as well be used dissolved in an aqueous solution containing 0.8 to 1 w/v %, preferably about 0.9 w/v %, of sodium chloride. If the salt concentration is too high, viscoelasticity decreases, and deformation when compressed increases. If the salt concentration is too low, the injection pressure becomes high.

In the injectable preparation of the present invention, optional components may be jointly used unless they impair the objects of the present invention. For example, there may be jointly used pigments, such as Indigo Carmine and Methylene Blue, for facilitating visual observation during injection, and pharmacodynamic components having a hemostatic action or a vasoconstrictive action, such as epinephrine, norepinephrine, and isoproterenol, for preventing bleeding during resection.

The injectable preparation of the present invention can be used by means of an endoscopic injection needle having a diameter of 20 to 22 G, preferably 21 G, and comprising an injection needle tube having an effective length of 1,000 mm or more, preferably 1,500 to 2,500 mm, particularly preferably 1,600 to 2,400 mm.

In the present invention, it is operationally preferred for the injectable preparation to be used while appropriately adjusted such that its injection pressure when injected by use of the above endoscopic injection needle is 0.5 to 4 atmospheres, preferably 2 to 3 atmospheres. In the present invention, moreover, it is operationally preferred for the injectable preparation to be used while appropriately adjusted such that its inflow rate when injected into a mucosal tissue at a pressure of 2 to 3 atmospheres by use of the above endoscopic injection needle is 0.05 to 0.1 ml/sec, preferably 0.07 to 0.09 ml/sec. The adjustment of the injectable preparation can be made by appropriately selecting the concentration of hyaluronic acid, the concentration of salt, and pH (appropriately adjusted within the pH range of 4.5 to 8.0).

The endoscopic injectable preparation of the present invention can be preferably used for resection of a mucosal tissue of the stomach or intestine. That is, the injectable preparation is injected through the endoscopic injection needle into a stratum beneath the mucosa scheduled for resection of a polyp or cancer to elevate the site to be resected, and then the elevated portion is resected with a snare (wire loop) or a needle knife.

In the present invention, even when an elevation time of 90 minutes has passed since injection, the elevated state is maintained. Moreover, deformation does not occur substantially even when the elevated site is compressed during resection. Thus, resection, in one piece, of a large mucosal site measuring 20 mm or more can be performed reliably and safely.

The present invention will be described in more concrete terms with reference to Examples, which in no way limit the present invention.

EXAMPLE 1

Injectable preparations to be described below were measured for inflow rates (ml/sec) when they were injected at a pressure of 3 atmospheres with the use of a 5 ml injection tube for an endoscopic injection needle which had a diameter of 21 G and whose tube had an effective length of 1,600 mm. The average of 5 stable measurements was calculated, and taken as the inflow rate.

Previously, the injection pressure had been actually measured using the above 5 ml injection tube, confirming 0.5 to 4 atmospheres, especially 2 to 3 atmospheres, to be the preferred injection pressure permitting injection without particular difficulty.

<Production Example of the Injectable Preparations>

(1) Low molecular weight hyaluronic acid (molecular weight of about 800,000) (hereinafter referred to as "HA80") was dissolved in an aqueous solution of 0.9 w/v % NaCl (pH about 6.0) to prepare an injectable preparation having a concentration of 0.5 w/v %.

(2-1 to 2-3) High molecular weight hyaluronic acid (molecular weight: about 1,900,000) (hereinafter referred to as "SVE") was dissolved in an aqueous solution of 0.9 w/v % NaCl (pH about 6.0) to prepare three injectable preparations having concentrations of 0.25 w/v %, 0.33 w/v %, and 0.4 w/v %. SVE is high molecular weight hyaluronic acid obtained by culturing *Streptococcus equi*.

<Results>

The inflow rates of the respective injectable preparations determined in the above-described manner were as follows:

TABLE 1

| Injectable preparation | Concentration (w/v %) | Inflow rate (ml/sec) |
|---|---|---|
| (1) | 0.5 | 0.08 |
| (2-1) | 0.25 | 0.225 |
| (2-2) | 0.33 | 0.13 |
| (2-3) | 0.4 | 0.08 |

The above experimental results showed that injection resistance comparable to that of low molecular weight hyaluronic acid at a concentration of 0.5 w/v %, a concentration permitting sufficient injection at a practically usable injection pressure, was obtained even by high molecular weight hyaluronic acid at a relatively close concentration of 0.4 w/v %.

EXAMPLE 2

Comparative Experiments on the Degree of Mucosal Elevation

Comparative experiments on the degree of mucosal elevation were conducted using a porcine resected stomach. It was investigated whether there would be differences in the degree and duration of mucosal elevation between 0.5 w/v % low molecular weight hyaluronic acid (HA80) and 0.4 w/v % high molecular weight hyaluronic acid (SVE), which had been confirmed by the above-described experiments to be comparable in injection resistance.

0.5 w/v % HA80, 0.4 w/v % SVE, and an aqueous solution of 0.9 w/v % NaCl (pH about 6.0) as a control were each injected submucosally in an amount of 1.5 ml. Mucosal elevations due to the injections were observed immediately after, 5 minutes after, 10 minutes after, 30 minutes after, 60 minute after, and 90 minutes after injection. The mucosal elevations were evaluated by the shapes of cross sections of the elevations observed visually (recorded photographically) and with an ultrasonic tomograph. The injection was performed using a 5 ml injection tube with an ordinary injection needle having a diameter of 21 G. The injection rate at that time was about 0.1 ml/sec. The same experiments were conducted twice, and the averages were calculated as the results.

<Results>

(a) Visual Evaluations

The steepness of the mucosal elevation by visual observation was expressed on a scale of (−) to (+++).

TABLE 2

| | Time elapsed after injection | | | | | |
|---|---|---|---|---|---|---|
| | Immediately | 5 min | 10 min | 30 min | 60 min | 90 min |
| Control | +++ | + | +− | +− | − | − |
| HA80 | +++ | +++ | ++ | ++ | + | + |
| SVE | +++ | +++ | +++ | +++ | +++ | +++ |

(b) Evaluations by Ultrasonic Tomograph

Using an ultrasonic tomograph (OLYMPUS), the height (longitudinal diameter: mm) and breadth (transverse diameter: mm) of a vertical cross section in a low echo area due to the liquid injected into the submucosal stratum below the mucosal elevation were measured at the above-mentioned predetermined time intervals. The ratio between the longitudinal diameter and the transverse diameter was calculated, and the values obtained in the respective samples were compared. The results are shown graphically in FIG. 1.

The above results showed that hyaluronic acid was superior to physiological saline, as a substance to be injected submucosally for inducing mucosal elevation. It was also shown that 0.4 w/v % high molecular weight hyaluronic acid produced by far better persistence of mucosal elevation than did 0.5 w/v % low molecular weight hyaluronic acid, although there was no difference between the two in injection resistance.

INDUSTRIAL APPLICABILITY

If the endoscopic injectable preparation of the present invention is used, it can be injected into a mucosal tissue at an operationally practical pressure, the site elevated by injection is maintained in a satisfactory elevated state even after a lapse of the elevation time of 90 minutes, and the site of elevation does not substantially deform when compressed during resection. Thus, the resection, in one piece, of a large mucosal site measuring 20 mm or more can be performed reliably and safely.

The invention claimed is:

1. A method comprising
    injecting a preparation into a predetermined mucosal tissue to elevate the mucosal tissue, and
    endoscopically resecting the mucosal tissue portion,
    wherein the preparation comprises a gelled high viscosity substance comprising 0.25 to 0.4 weight/volume percent of hyaluronic acid having a viscosity-average molecular weight of 1,900,000 to 2,200,000 or a salt thereof, the gelled high viscosity substance is dissolved in an aqueous solution containing 0.8 to 1 weight/volume percent of sodium chloride, and the preparation is injected through an injection needle having a diameter of 20 to 22 G, and an effective length of a tube of the injection needle is 1,000 mm or more such that the inflow rate of the injectable preparation, when injected at a pressure of 2 to 3 atmospheres through said injection needle, is 0.05 to 0.1 ml/sec.

2. The method according to claim 1, wherein the gelled high viscosity substance comprises said hyaluronic acid obtained by microbial fermentation.

3. The method according to claim 2, wherein the hyaluronic acid is a product of microbial fermentation of *Streptococcus equi*.

4. The method according to claim 1, wherein the preparation is injected at a pressure of 0.5 to 4 atmospheres.

* * * * *